United States Patent [19]

Verson

[11] Patent Number: 4,868,342
[45] Date of Patent: Sep. 19, 1989

[54] ALKYLATION AND DEHYDROGENATION PROCESS FOR THE PRODUCTION OF PROPYLENE AND HIGH OCTANE COMPONENTS

[75] Inventor: Ronald L. Verson, Glenview, Ill.

[73] Assignee: UOP, Des Plaines, Ill.

[21] Appl. No.: 164,262

[22] Filed: Mar. 4, 1988

[51] Int. Cl.$^4$ .......................... C07C 41/06; C07C 2/58
[52] U.S. Cl. ..................................... 568/697; 585/324; 585/331
[58] Field of Search ................. 585/324, 331; 568/697

[56] References Cited

U.S. PATENT DOCUMENTS

| | | | |
|---|---|---|---|
| 3,172,834 | 3/1965 | Kozlowski | 208/58 |
| 3,484,497 | 12/1969 | Berger | 260/671 |
| 3,992,474 | 11/1970 | Sobel | 260/683.48 |
| 4,324,937 | 4/1982 | Vora | 585/315 |
| 4,523,048 | 6/1985 | Vora | 585/323 |
| 4,695,662 | 9/1987 | Vora | 585/324 |

*Primary Examiner*—Howard T. Mars
*Attorney, Agent, or Firm*—Thomas K. McBride; John G. Tolomei

[57] ABSTRACT

A process for the production of propylene and high octane blending components from $C_3$ and $C_4$ hydrocarbons that provides the dual benefit of flexibility between alkylate and propylene products while allowing the processing of large amounts of normal butane. The process includes the steps of passing a combined feed of $C_3$ and $C_4$ hydrocarbons to a dehydrogenation zone, contacting the feed stream with a dehydrogenation catalyst, and recovering an effluent containing $C_3$ and $C_4$ olefins and admixing the effluent with another feed comprising paraffins and olefins having from 3–4 carbon atoms and recovering an intermediate stream. The intermediate stream enters a separation zone, which removes $C_2$ hydrocarbons and lower boiling materials from the process, recovers a first propylene product stream, produces an alkylation zone feed stream containing $C_3$ and $C_4$ hydrocarbons, and produces a recycle stream. The alkylation zone feed is combined with make-up isobutane and enters an alkylation zone to produce an alkylation zone effluent containing high octane blending components comprising $C_7$ and $C_8$ hydrocarbons. After separating the alkylation zone effluent into the $C_7$ and $C_8$ product stream and a recycle stream rich in normal butane, the normal butane-rich recycle stream is combined with the propane recycle and a $C_4$ paraffin stream to form the feed to the dehydrogenation zone. Additional products may be obtained by passing the alkylation zone feed first through an etherification zone and then into the alkylation zone.

15 Claims, 2 Drawing Sheets

ALKYLATION AND DEHYDROGENATION PROCESS FOR THE PRODUCTION OF PROPYLENE AND HIGH OCTANE COMPONENTS

FIELD OF THE INVENTION

This invention relates generally to the conversion of $C_3$ and $C_4$ hydrocarbons. More specifically, this invention is a process for upgrading $C_4$ and $C_3$ hydrocarbons into high value products such as propylene and high octane blending components for motor fuels.

BACKGROUND OF THE INVENTION

Uncertainties in the purchase price, selling price, and availability of various petrochemical feedstocks and products have plagued the refining industry. One particular area of volatility and uncertainty is in the processing of $C_3$ and $C_4$ hydrocarbon feedstocks. $C_3$ hydrocarbons can be used as fuels with little processing or refined and separated to recover more valuable products such as propylene. The conversion of $C_3$ products to propylene is usually preferred, however, variations in the price for propylene and the cost of large stand-alone conversion units have discouraged refiners from investment in large scale facilities dedicated to the production of propylene alone. $C_4$ hydrocarbons find widespread use as direct additives to motor fuel due to their relatively high octane and relatively low price. However, the direct addition of $C_4$ hydrocarbons is limited by gasoline vapor pressure considerations which may be restricted further in the near future by pending government legislation. These considerations affect the processing of field butanes containing a relatively high amount of normal butanes making it more economically desirable to convert these to alkylate.

$C_4$ hydrocarbons and $C_3$ hydrocarbons may be converted to higher molecular weight and higher octane branched paraffins by alkylation. A typical alkylation zone can react butenes or porpylene with isobutane to obtain highly branched $C_7$ or $C_8$ isomers. $C_4$ hydrocarbons are also commonly used to synthesize additives such as MTBE that have low vapor pressure and high octane. In light of these uncertainties and a variation in supply and demand for feedstocks and products, it would be highly desirable to have a process for converting $C_3$ and $C_4$ hydrocarbons that provide propylene product or alkylate blending components in varying proportions while at the same time facilitating the operation of the alkylation process and the production of propylene. The ability to produce MTBE as another alternative product would be an added benefit of such a process.

As the value of product propylene by itself rises and regulations restrict the direct blending of butane in motor fuels, it is also highly useful to have a process that can recover increased quantities of propylene directly as product and can also process additional butanes into higher molecular weight and relatively low vapor pressure motor fuel components. It would also be highly beneficial that the process can be integrated into existing alkylation facilities.

INFORMATION DISCLOSURE

U.S. Pat. No. 3,484,497 shows a process for the production of alkylaromatic hydrocarbons. The process shows a dehydrogenation zone, a separation zone, and an alkylation zone in series for dehydrogenating a normal paraffin feed, recycling unreacted feed components to the dehydrogenation zone and passing unsaturated dehydrogenation products to an alkylation zone.

U.S. Pat. No. 3,992,474 teaches the use of an FCC unit to produce olefins from the low octane recycle component of an alkylation process and the delivery of the FCC product to the alkylation zone.

U.S. Pat. No. 4,324,937 discloses an integrated process for the conversion of $C_3$ and $C_4$ hydrocarbons into high octane blending stocks. A feed of $C_3/C_4$ hydrocarbons enters a splitter that divides the feed into $C_3$ and $C_4$ components. The $C_3$ component enters a propane dehydrogenation zone. The $C_4$ components enter an isostripper that provides butanes to an isomerization zone, receives isobutanes from the isomerization zone, and separates the product from an isomerization zone. The isostripper also separates $C_5$ and higher hydrocarbons for recovery as a product stream, provides an isobutane side cut, and provides an overhead of mixed $C_4$ and lighter hydrocarbons. Overhead from the isostripper enters a fractionation zone which removes propane and light hydrocarbons for recycle to the propane dehydrogenation zone and provides a $C_4/C_3$ feed fraction for the alkylation zone. Effluent from the propane dehydrogenation passes through a deethanizer for the removal of light ends and is combined with the $C_4/C_3$ feed fraction and isostripper side cut to provide the feed to the alkylation zone.

U.S. Pat. No. 4,523,048 is directed to a process for producing alkyl benzenes. The process has in series a dehydrogenation zone for generating $C_{10}$-$C_{15}$ olefins, a selective hydrogenation zone for eliminating diolefins, alkylation zone for producing linear alkyl benzene, generally known as detergent alkylate, and a fractionation zone. A linear alkyl benzene product stream, a benzene recycle stream for return to the isomerization zone, and a paraffinic recycle stream that reenters the dehydrogenation zone are recovered from the fractionation zone.

U.S. Pat. No. 4,695,662 depicts a light paraffinic hydrogenation process that passes isobutane and propane through a dehydrogenation reactor and separates the effluent of the dehydrogenation into $C_3$ and $C_4$ streams. Propylene is separated from the $C_3$ stream and a remaining propane-rich stream reenters the dehydrogenation zone. The process charges the $C_4$ stream or at least an isobutene-rich fraction thereof to an etherification zone.

U.S. Pat. No. 3,172,834 presents a method of processing a hydrocracking reaction zone effluent by recovering $C_3$ and $C_4$ hydrocarbons, passing a portion of the $C_3$ and $C_4$ hydrocarbons to a dehydrogenation zone and combining the dehydrogenation zone effluent with additional $C_4$'s to create a feed to an alkylation zone.

It has now been discovered that $C_3/C_4$ dehydrogenation process and its separation facilities can be integrated with an alkylation process to an arrangement for processing of $C_3$ and $C_4$ hydrocarbons that will increase the product yield of propylene, produce a high molecular weight and high octane alkylate product, and provide facilities for the increased conversion of butanes.

BRIEF SUMMARY OF THE INVENTION

Therefore, it is an object of this invention to provide a process for obtaining propylene and high octane, low vapor pressure, blending components from $C_3$ and $C_4$ feedstocks that can be adjusted with varying demands of propylene and alkylate products and varying availability of $C_3$ or $C_4$ hydrocarbons.

A further object of this invention is the integration of a process for the dehydrogenation of $C_3$ and $C_4$ hydrocarbons and a process arrangement for producing propylene and high octane blending components as products.

It is a further object of this invention to remove $C_3$ hydrocarbons from the feed to an alkylation zone while obtaining additional valuable products.

A yet further object of this invention is to use an HF alkylation zone for $C_4$ conversion which also separates normal butanes to provide a normal butane feed component to a dehydrogenation process that in turn supplies butenes to the alkylation zone.

Thus, this invention, in a general sense, is a process for dehydrogenating $C_3$ and $C_4$ hydrocarbons which are then combined with a mixed stream of $C_3$ and $C_4$ olefins and paraffins, passed through separation facilities for the dehydrogenation zone which are used to recover a high grade propylene product, provide propane recycle to the dehydrogenation zone, and generate a mixed stream of primarily normal butane, isobutane, and butenes for an alkylation zone. The alkylation zone reacts out the butenes and isobutane thereby providing additional butane recycle for the dehydrogenation zone and high molecular weight alkylate product having an increased octane number relative to a $C_3/C_4$ alkylation process due to the prior removal of $C_3$ hydrocarbons.

Accordingly, in one embodiment, this invention is a process for deriving propylene and high octane blending components from $C_3$ and $C_4$ hydrocarbons. In the process, a first feed stream containing $C_3$ and $C_4$ hydrocarbons is passed to the dehydrogenation zone where the feed stream is contacted with the dehydrogenation catalyst at dehydrogenation conditions to produce a first effluent having an increased concentration of $C_3$ and $C_4$ olefins relative to the feed stream. An intermediate stream is formed by admixing the first effluent with a second feed stream that contains paraffins and olefins having from 3-4 carbon atoms. The intermediate stream passes through a separation zone that recovers a first product stream consisting essentially of propylene, produces a third feed stream comprising $C_3$ and $C_4$ hydrocarbons and provides a first recycle stream comprising propane. The third feed stream enters an alkylation zone, which also receives a fourth feed stream comprising isobutane, and therein contacting the third and fourth feeds with an alkylation catalyst at alkylation conditions to produce a second effluent that contains high octane blending components having from 7-8 carbon atoms. The second effluent passes through separation facilities that recover a second product stream containing the $C_7$ and $C_8$ hydrocarbons and a second recycle stream that is rich in normal butane. The first recycle stream, the second recycle stream, and a fifth feed stream of $C_4$ paraffins are combined to form the first feed stream.

In a further embodiment this invention is a process for producing propylene and high octane blending components including $C_7$-$C_8$ alkylates and ethers. In the process a first recycle stream, a second recycle stream, and a stream of $C_4$ paraffins are combined to form a first feed stream. The first feed stream enters a dehydrogenation zone where it is contacted with a dehydrogenation catalyst at dehydrogenation conditions to produce a first effluent comprising $C_3$ and $C_4$ olefins and paraffins. The first effluent is mixed with a second feed stream comprising $C_3$ and $C_4$ hydrocarbons which are transferred in admixture to a selective hydrogenation zone that contacts the streams with a selective hydrogenation catalyst at selective hydrogenation conditions to produce a second effluent stream substantially free of diolefins. The second effluent stream enters a depropanizer that recovers a third feed stream which is rich in $C_4$ hydrocarbons. The remainder of the second effluent from the depropanizer enters a propane/propylene splitter that provides a first product stream of high purity propylene and the first recycle stream that comprises propane. The third feed stream and a feed of $C_1$-$C_5$ monohydric alcohol are passed to an etherification zone where the alcohol and the third feed are contacted with an etherification catalyst at etherification conditions to provide a third effluent from the etherification zone. The third effluent is separated into a second product stream made up of high octane ether and the remainder of the effluent is passed through an oxygenate removal zone. The remaining portion of the third effluent is recovered from the oxygenate removal zone and passed with a fourth feed stream comprising isobutane to an alkylation zone where the streams are contacted with an alkylation catalyst at alkylation conditions to recover a fourth effluent stream. The fourth effluent stream is separated into the second recycle stream that comprises $C_3$ and $C_4$ normal hydrocarbons and a third product stream made up of primarily branched $C_7$ and $C_8$ paraffins.

Other aspects and embodiments of this invention relate to stream compositions, separation methods, catalysts, etc.

DETAILED DESCRIPTION OF THE INVENTION

In its most basic form, this invention uses a dehydrogenation zone, a separation zone, and an alkylation zone that complements the function of the separation zone by reacting out butenes and forming normal butane recycle stream. The separation facilities also complement the operation of the alkylation process by reducing the quantity of $C_3$ hydrocarbons that enter the feed to the alkylation zone, while at the same time, facilitating the conversion of propane to high value propylene products. At least three different feed streams of $C_3$ and/or $C_4$ hydrocarbons are added to the process at different locations which have been found to allow the process to function with reduced equipment and capital cost. Other important methods of operating this invention include the addition of a selective hydrogenation process and/or the addition of etherification facilities. Details of these arrangements and methods of operation will be described in the context of FIGS. 1 and 2.

Looking at FIG. 1, a feed stream of C hydrocarbons enters the process via line 10 where it is combined with the hereinafter described recycle stream from line 12. The feed stream of line 10 will be rich in saturated $C_4$ hydrocarbons. The term "rich" as used throughout the specification means a stream composition containing more than 50 mol % of the material denoted as rich. A high concentration of saturated hydrocarbons is preferred to increase the conversion within the hereinafter described dehydrogenation zone. Ordinarily, this feed stream will contain some mixture of isobutane and normal butane. Typical sources for this feed stream are field butanes and other $C_4$ hydrocarbon streams including refinery saturated butanes.

A line 14 carries the combined recycle stream and feed stream into a dehydrogenation zone 16. The dehydrogenation zone of this invention can consist of any dehydrogenation process for the production of olefins from saturated $C_3$-$C_4$ hydrocarbons. Preferably, the dehydrogenation process will produce only monoolefins. It is also preferred that the dehydrogenation be capable of converting at least 50% of the saturated hydrocarbons passing therethrough to monoolefins. A relatively high saturate conversion in the dehydrogenation specification reduces the necessary, downstream separation facilities including those associated with the hereinafter described alkylation zone.

Along with the $C_3$/$C_4$ dehydrogenatable hydrocarbons, the feed to the dehydrogenation zone of the present invention comprises an $H_2$ rich stream, preferably containing at least 75 mol % $H_2$. The presence of $H_2$ within the dehydrogenation zone serves several purposes. First, the $H_2$ acts to suppress the formation of hydrocarbonaceous deposits on the surface of the catalyst, more typically known as coke. Secondly, $H_2$ can act to suppress undesirable thermal cracking. Because $H_2$ is generated in the dehydrogenation reaction and comprises a portion of the effluent, the $H_2$ rich stream introduced into the reaction zone generally comprises recycle $H_2$ derived from separation of the dehydrogenation zone effluent. Alternately, the $H_2$ may be supplied from suitable sources other than the dehydrogenation zone effluent. The embodiment of FIG. 1 uses internally recirculated hydrogen and shows hydrogen generated in the process being withdrawn by line 18.

The dehydrogenatable hydrocarbon stream and $H_2$ stream are introduced into a dehydrogenation reaction zone. The dehydrogenation reaction zone of this invention preferably comprises at least one radial flow reactor through which the catalytic composite gravitates downwardly to allow a substantially continuous replacement of the catalyst with fresh and/or regenerated catalyst. A detailed description of the moving bed reactors herein contemplated may be obtained by reference to U.S. Pat. No. 3,978,150. The dehydrogenation reaction is a highly endothermic reaction which is typically effected at low (near atmospheric) pressure conditions. The precise dehydrogenation temperature and pressure employed in the dehydrogenation reaction zone will depend on a variety of factors such as the composition of the paraffinic hydrocarbon feedstock, the activity of the selected catalyst, and the hydrocarbon conversion rate. In general, dehydrogenation conditions include a pressure of from about 0 to about 35 bars and a temperature of from about 480° C. (900° F.) to about 760° C. (1400° F.). The $C_3$ and $C_4$ hydrocarbons are charged to the reaction zone and contacted with the catalyst contained therein at a liquid hourly space velocity of from about 1 to about 10. Hydrogen, principally recycle hydrogen, is suitably admixed with the hydrocarbon feedstock in a mole ratio of from about 0.1 to about 10. Preferred dehydrogenation conditions, particularly with respect to $C_3$-$C_4$ paraffinic hydrocarbon feedstocks, include a pressure of from about 0 to about 20 bars and a temperature of from about 540° C. (1000° F.) to about 705° C. (1300° F.), a liquid hourly space velocity of from about 1 to about 5, and a hydrogen/hydrocarbon mole ratio of from about 0.5 to about 2.

The dehydrogenation zone of this invention may use any suitable dehydrogenation catalyst. Generally, the preferred catalyst comprises a platinum group component, an alkali metal component, and a porous inorganic carrier material. The catalyst may also contain promoter metals which advantageously improve the performance of the catalyst. It is preferable that the porous carrier material of the dehydrogenation catalyst be an absorptive high surface area support having a surface area of about 25 to about 500 $m^2$/g. The porous carrier material should be relatively refractory to the conditions utilized in the reaction zone and may be chosen from those carrier materials which have traditionally been utilized in dual function hydrocarbon conversion catalysts. A porous carrier material may, therefore, be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxides such as alumina, titanium dioxide, zirconium dioxides, magnesia, silica alumina, alumina boria, etc.; crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/10 inch.

The preferred dehydrogenation catalyst also contains a platinum group component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or an elemental metal or in combination with one or more other ingredients of the catalyst. It is believed that the best results are obtained when substantially all the platinum group components exist in the elemental state. The platinum group component generally comprises from about 0.01 to about 2 wt. % of the final catalytic composite, calculated on an elemental basis. It is preferred that the platinum content of the catalyst be between about 0.1 and 1 wt. %. The preferred platinum group component is platinum, with palladium being the next preferred metal. The platinum group component may be incorporated into the catalyst composite in any suitable manner such as by coprecipitation or coagulation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

Additionally, the preferred catalyst contains an alkali metal component chosen from cesium, rubidium, potassium, sodium, and lithium. The preferred alkali metal is normally either potassium or lithium, depending on the feed hydrocarbon. The concentration of the alkali metal may range from about 0.1 to 5 wt. %, but is preferably between 1 and about 4 wt. % calculated on an elemental basis. This component may be added to the catalyst by the methods described above as a separate step or simultaneously with the solution of another component. With some alkali metals, it may be necessary to limit the halogen content to less than 0.5 wt. % and preferably less than 0.1 wt. %, while others may have higher halogen content.

As noted previously, the dehydrogenation catalyst may also contain promoter metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. Thus, the component may be added to the carrier by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

Effluent from the dehydrogenation reaction section is combined with additional $C_3/C_4$ hydrocarbons from line 17 and passed directly to a second separation section. The feed added at this point can be a $C_3/C_4$ mixture containing substantial portions of olefins and isobutane. The $C_3/C_4$ cut from an FCC unit is a particularly preferred source for such feed since it typically contains substantial amounts of propylene which can be recovered as an additional product and isobutane and butenes that are needed reactants for the alkylation zone.

However, many of the dehydrogenation processes that can be used in this process will produce some quantity of dienes and acetylenes. These compounds are extremely unstable and their presence in motor fuel is objectionable. Furthermore, when, as in this invention, the dehydrogenation zone effluent will be further processed in additional catalytic reaction zones, the diolefins and acetylenic hydrocarbons can foul catalyst and interfere with the operation of the process by reacting with each other or other hydrocarbons to form coke and hydrogen deficient polymers that are absorbed on to the surface of the catalyst. In particular, where diolefins are present in a hydrofluoric acid (HF) alkylation process, they tend to form high boiling hydrocarbons that increase the rate of HF acid consumption. Therefore, for purposes of product quality and process operation, a selective hydrogenation zone is a desirable additional feature of this invention. An added advantage of using a selective hydrogenation zone is the known ability of some such processes to isomerize butene-1 to butene-2. Butene-2 is a more desired feed to the alkylation zone since it forms higher octane components such as 2,2,4-trimethylpentane. However, where acid consumption in the alkylation unit is not a concern and the specifications for the propylene product allow some acetylenic and diolefinic materials, a selective hydrogenation process may not be required. Where diolefins pose concern about acid consumption but are not a concern from the standpoint of propylene product specifications, the selective hydrogenation zone may be placed just ahead of the alkylation zone to process only the feed to the alkylation zone.

Figure 1:
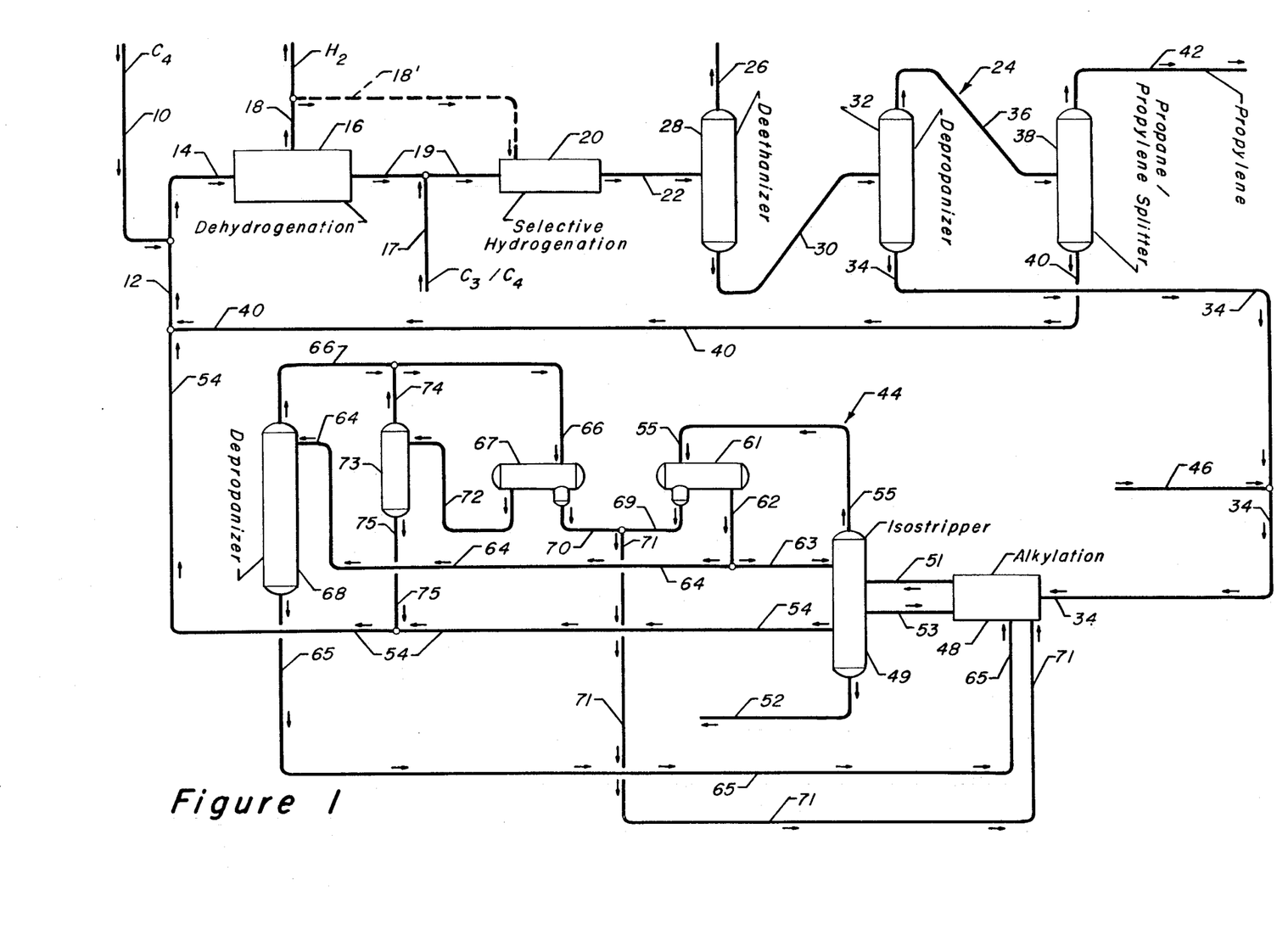
FIG. 1 shows a flow scheme for the process of this invention that incorporates a dehydrogenation zone, selective hydrogenation zone, separation facilities, and an alkylation zone.

FIG. 1 shows a line 19 passing the effluent from dehydrogenation zone 16 and, an additional $C_3/C_4$ feed from a line 17, to a selective hydrogenation zone 20. A wide variety of selective hydrogenation processes are in commercial use. The only requirements for the selective hydrogenation zone of this invention is that it have the generally desirable features of operating at mild conditions, yielding a low amount of lighter hydrocarbons, and minimizing monoolefin loss.

Selective hydrogenation processes are normally performed at relatively mild hydrogenation conditions. Typically, these conditions will keep the hydrocarbons in liquid phase. Thus, the reactants will normally be maintained under the minimum pressure sufficient to maintain the reactants as liquid phase hydrocarbons. A broad range of suitable operating pressures, therefore, extends from about 40 to about 800 psig (276–5516 kPag), with a pressure between about 50 and 300 psig (345–2069 kPag) being preferred. A relatively moderate temperature between about 25° and about 350° C. (77° and 662° F.) should be employed. Preferably, the temperature of the hydrogenation zone is maintained between about 50° and about 200° C. (122° and 392° F.). The liquid hourly space velocity of the reactants through the selective hydrogenation catalyst should be above 1.0. Preferably, it is above 5.0 and more preferably it is between 5.0 and 35 hrs$^{-1}$. Another variable operating condition is the ratio of hydrogen to diolefinic hydrocarbons maintained within the selective hydrogenation zone. The amount of hydrogen required to achieve a certain conversion is believed dependent upon both reactor temperature and the molecular weight of the feed hydrocarbons. To avoid the undesired saturation of a significant amount of monoolefins hydrocarbons, there should be less than 2.0 times the stoichiometric amount of hydrogen required for the selective hydrogenation of the diolefinic hydrocarbons which are present in the liquid phase process stream to monoolefinic hydrocarbons. Preferably, the mole ratio of hydrogen to diolefinic hydrocarbons in the material entering the bed of selective hydrogenation catalyst is maintained between 1:1 and 1.8:1. In some instances, it may be desirable to operate with a less than stoichiometrically required amount of hydrogen, with mole ratios down to 0.75:1 being acceptable. The optimum set of conditions will, of course, vary depending on such factors as the composition of the feed stream and the degree of saturation of diolefinic hydrocarbons which it is desired to perform. Nevertheless, since the amount of diolefins in the reactants is small, the hydrogen requirements are easily fulfilled. As FIG. 1 shows, a small sidestream 18' of net hydrogen from line 18 supplies the necessary hydrogen for the hydrogenation zone.

The selective hydrogenation process typically uses a fixed bed reactor containing a cylindrical bed of catalyst through which the reactants move in a vertical direction. It is preferred that the reactants flow upward through the reactor as this provides goo mixing.

A preferred form of the catalytic material is an alumina support material containing from 0.15 to 0.85 wt. % tin, about 4.0 to 25 wt. % nickel, and about 0.1 to 1.5 wt. % sulfur which is essentially free of platinum metals. The catalytic material can be in a variety of shapes but, spheres having a diameter between about 1/64th and ¼ of an inch are preferred. It is greatly preferred that the spherical alumina particles are formed by a method for effecting gelation of a tin-containing alumina sol such as described in U.S. Pat. No. 2,620,314 issued by J. Hoekstra. The alumina sol may be formed a number of different ways. A typical one is to digest aluminum metal with an aqueous solution of approximately 12% hydrogen chloride to produce an aluminum chloride sol. Another method comprises electrolysis of a solution of aluminum chloride in an electrolytic cell. A common method of preparing an alumina sol is the addition of aluminum metal to an aqueous solution of aluminum chloride with this mixture being subjected to heating and digesting at its boiling point. To effect the addition of the tin component to the desired catalyst, a solubilized tin compound is normally admixed into the acidic alumina sol. A detailed description of the information of tin-containing alumina sols is provided in U.S. Pat. No. 3,926,849. An acid salt of tetravalent tin has been described as most useful for the addition of the tin component. A method for effecting the gelation of the tin containing sol comprises the steps of admixing the sol with a gelling agent at a temperature below the gelation temperature and then dispersing the resulting admixture as droplets in a hot oil bath whereby gelation occurs with the formation of firm spherical gel particles. The alumina hydrogel spheres are then subjected to certain aging treatments in order to impart the desired physical characteristics.

The nickel component could be added to the catalyst during the sphere formation procedure in a manner similar to the addition of tin if it is so desired. However, it is greatly preferred that the nickel component of the catalyst is added to the previously formed alumina spheres as by an impregnation technique in which the formed alumina spheres are immersed into a solution of a nickel compound. Preferably, the formed calcined alumina spheres are immersed in an aqueous solution of nickel acetate, nickel sulfate or nickel nitrate or other water soluble nickel compound. The solution is then preferably evaporated to dryness in contact with the spheres utilizing a rotary steam evaporator. The dried particles may then be calcined at a temperature of about 150° C. for one hour and then at about 525° C. for one hour. The formed spheres may then be dried and purged with nitrogen and are preferably subjected to a reduction step in contact with a hydrogen-containing gas.

The sulfur component is preferably added to the catalytic composite in a final preparation step after the formation of a tin-containing alumina base and the placement of the nickel upon the alumina base material to place substantially all of the sulfur on the available surface of the catalyst. In this sulfiding procedure, the initial composite is subjected to sulfiding conditions sufficient to provide the desired sulfur concentration. Sulfiding may be performed under liquid phase conditions, however, it is greatly preferred to perform this step at vapor phase conditions. It is, therefore, preferred to deposit the sulfur component upon the catalyst by contacting the initial composite with a vaporous sulfur-containing compound. Preferably, the sulfur-containing compound is present in admixture with hydrogen. A preferred sulfur-containing or sulfur yielding compound is hydrogen sulfide. Other sulfur or sulfide yielding compounds which may be employed for this purpose include ammonium sulfide, ammonium hydrosulfide, the alkyl and aryl mercaptans, organic thioethers, disulfides thioaldehydes and other sulfur-yielding organic compounds. The sulfiding conditions preferably include a temperature sufficient to maintain the sulfiding compound present as a vapor, with these temperatures ranging from about 10° to about 500° C. The composition of the preferred hydrogenation catalyst is also specific as to those compounds which are not present within the catalytic composite. The catalyst is essentially free of the noble or platinum group metals which include platinum, palladium, rhodium, and iridium. Preferably, the catalyst is essentially free of all Group VIII metals except for nickel. Therefore, the catalyst is essentially free of iron and cobalt. Furthermore, the catalytic composite is preferably also essentially free of the alkaline earth metals, of which calcium, strontium, and barium are the most common. The catalytic composite is preferably also essentially free of the alkali metals of which lithium, sodium, and potassium are the most commonly used catalyst components. Finally, the catalytic composite is preferably essentially free of the halogens including fluorine, chlorine, bromine and iodine. The effluent from the selective hydrogenation zone is carried by a line 22 to a separation section 24. Before passing out of the selective hydrogenation zone by line 22, a number of separation steps may be performed for the recovery of hydrogen including the cooling and compressing with subsequent flashing in a separation vessel. Hydrogen recovered in the step may be recycled to the selective hydrogenation zone to provide a portion of the hydrogen requirements for the process. Separation zone 24 divides the effluent stream 22 into a minimum of four process streams. These four streams, produced by the separation zone consist of light ends, a feed stream to the alkylation zone, a propylene product, and a propane recycle stream. In FIG. 1, the light gas stream is shown being removed as an overhead stream 26 from a deethanizer column 28. When a selective hydrogenation zone is used in the process, it is also possible to have deethanizer column between the dehydrogenation zone and selective hydrogenation zone for eliminating light hydrocarbons. In such cases there will be no need to provide the deethanizer after the selective hydrogenation zone.

FIG. 1 shows separation zone 24 schematically with a three column arrangement. Again effluent from the selective hydrogenation zone enters the deethanizer column 28 from which the light gas stream is withdrawn as an overhead by line 26. Line 30 carries the bottom stream of heavier material from column 28 to a depropanizer column 32. $C_4$ hydrocarbons making up the alkylation zone feed are recovered by line 34 from the bottom of column 32. This feed stream will contain essentially all of the $C_4$ hydrocarbons entering the separation zone and whatever $C_3$ hydrocarbons may be separated therewith. If desired, additional $C_3$ hydrocarbons can be taken with the alkylation zone feed in an effort to balance the capacity of the alkylation zone and dehydrogenation facilities. In this way, propylene can be reacted to alkylate and eliminated from the propane recycle while propane may be recovered as a separate product. However, it is usually preferred to convert the propane to propylene product and use any additional alkylation capacity for the conversion of $C_4$ hydrocarbons. The remaining $C_3$ hydrocarbons pass overhead via line 36 to propane/propylene splitter 38. A bottom stream 40 delivers propane from the propane/propylene splitter back to line 12 and a propylene product is withdrawn overhead from splitter 38 by line 42. The separation zone is generally designed to provide a propylene stream of high purity. In order to restrict the size and complexity of the propylene recovery section, some percentage of propylene will be carried with the propane recycle stream. The propylene concentration in the propane recycle stream will vary with the desired purity of the propylene product.

Line 34 carries the mixed stream of butenes, normal butane and isobutane along with small amounts of $C_3$ hydrocarbons to an alkylation zone 44. The hydrocarbons carried by line 34 will usually contain an insufficient quantity of isobutane for allowing the maximum conversion of butenes in the alkylation zone. Therefore, additional isobutane is added via line 46 to the alkylation zone as another feed. This isobutane stream is generally of high purity and will normally have a concentration of at least 80 mol % isobutane, and more preferably, it will have a concentration exceeding 90 mol % isobutane. Any available source for this isobutane can be used, however, it is anticipated that in most refineries this isobutane will be from an external source. Where isostripper capacity is not a problem, the make-up isobutane can be obtained from field butanes that pass through the alkylation zone isostripper for separation of normal butanes. Alternately, a field butane stream may be diisobutanized to provide make-up isobutane.

Line 34 transfers the $C_3$ and $C_4$ paraffin feeds into a reactor section 48 of the alkylation zone. Although any type of alkylation reaction can be used, it is anticipated that an HF alkylation type process will be employed. In this type of process, the feed entering the alkylation reactor section should be dry and have a low sulfur content in order to reduce acid consumption and improve the quality of alkylate products. Water is eliminated since it causes corrosion problems in the acid environment of this type of alkylation process.

Methods for treating feeds for sulfur removal are well known. Standard practice for drying the feed has employed desiccant drying systems. As an alternative to the desiccant or other drying system, an alkylation feed stripper may also be used to dry the entire feed passing to the alkylation reactor.

The alkylation reaction is promoted by the presence of a mineral acid catalyst, in this case hydrofluoric acid. The acid is maintained in a liquid phase containing a minimum of water. The maximum amount of water normally allowed in the acid is about b 5 wt. %. When fresh acid is charged to a plant, it is normally very dry and contains about 0.5% water or less.

Alkylation conditions in general include a pressure sufficient to maintain the hydrocarbons and acid in a liquid phase, with a general range being from about 140 kPag (20 psig) to about 3500 kPag (500 psig), and a more preferred range being from 700 kPag (100 psig) to about 1700 kPag (250 psig). It is preferred that the pressure within the reactant-catalyst contacting vessel is approximately 1050 kPag (150 psig) and essentially "floats" on the pressure maintained in downstream fractionation facilities. Although the alkylation reaction may be performed at temperatures from below $-18°$ C. ($-4°$ F.) to about 90° C. (195° F.), it is preferred to operate the commercially prevalent isoparaffin-olefin alkylation process in the range of from about 10° C. (50° F.) to about 60° C. (140° F.), with 32° C. (90° F.) being a representative and particularly preferred operating temperature.

Typically operating conditions in the alkylation zone include a high ratio of the concentration of the paraffinic or other alkylatable material to the concentration of the olefinic material in order to produce a high quality alkylate by encouraging monoalkylation instead of polymerization. A broad range for this ratio is from about 6 to about 20 with a preferred operating range being from 7 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.2:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They would, however, have substantial differences in equipment and flow paths used in performing the alkylation. These variations are attempts to obtain optimum quality alkylate by varying the method of contacting the monoolefin with the isoparaffin. Since this reaction occurs very rapidly, and also because hydrofluoric acid will catalyze the polymerization of the monoolefin, the standard alkylation method consists of first admixing acid-free streams of olefin and isoparaffin to form a reactant mixture which is then admixed with the hydrofluoric acid. In this operation, a large number of venturies or mixing nozzles (not shown) are normally utilized to quickly disperse the olefin-containing stream into the acid-containing stream.

The resulting alkylation reaction is very exothermic and it is, therefore, necessary to provide means to remove the heat of reaction. This is normally done either by providing indirect heat exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler of reactor section 48 is passed into an isostripper 49 by a line 51. This hydrocarbon phase will comprise mainly alkylate and the excess isoparaffin which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., are well known to those skilled in the art.

Isostripper 49 is essentially the same as that normally associated with HF catalyst motor fuel alkylation units. The isostripper recovers the alkylate product along with small amounts of $C_4$ and $C_5$ hydrocarbons which are removed from the isostripper by line 52 as a net bottoms stream. The alkylate product in this invention is usually predominated by $C_8$ hydrocarbons but includes $C_6$–$C_9$ hydrocarbons as well. HF is used as the alkylation catalyst, the bottoms stream contains a small amount of isopentane brought in with the feeds or produced in the alkylation zone. Some propane is also produced in the alkylation zone in this instance. Isobutane and normal butane are withdrawn from the isostripper as an upper side cut by line 53 for recycle to the alkylation zone. In order to maintain the necessary isobutane to olefin ratio, line 56 will usually contain at least 60% isobutane. Normal butane is withdrawn from the isostripper by line 54 to provide the aforementioned recycle stream. When HF is utilized as the catalyst in the alkylation zone, fluoride compounds will normally be present in these output streams. These streams should then be passed through a fluoride removal zone comprising an alumina treater and a caustic contacting zone. Propane and HF acid are withdrawn with an overhead stream 55 from the isostripper.

Overhead stream 55 from the isostripper is condensed and charged to propane and acid recovery facilities usually start with an acid drum 61. Hydrocarbons from acid drum 61 are taken by line 62 and split into a reflux stream 63 for the isostripper and a stream 64 that enters a depropanizer 68. The depropanizer bottoms containing primarily $C_4$ and heavier hydrocarbons are returned to the reaction zone by line 65 while propane and lighter hydrocarbons are carried overhead by line 66 to acid drum 67. HF acid taken from the boot of drums 61 and 67, respectively by lines 69 and 70, is combined and returned to the reactor via line 71. A line 72 carries propane, some heavier hydrocarbons and small amounts of HF acid to an HF stripper 73. A line 74 returns additional acid from stripper 73 to overhead line 66. Propane from the HF stripper is combined with the principally isobuane stream 54 by line 75.

The process of this invention is particularly beneficial when it makes use of alkylation facilities in a refinery that were used to process $C_4$ feedstocks containing relatively large amounts of $C_3$ hydrocarbons. However, in such cases, the capacity of the isostripper may limit the amount of $C_4$ hydrocarbons that can be separated for recycle to the dehydrogenation zone and reaction zone. Any bottleneck posed by an existing isostripper is overcome, at least in part, by maintaining a high purity for the isobutane added to the alkylation zone through line 46. The addition of a high purity isobutane stream facilitates the separation of iso and normal butane in the existing isostripper thus, assisting in obtaining the desired isobutane to olefin ratio in the reaction zone. For these purposes, the purity of the isobutane stream would normally be greater than 90 mol %.

The alkylation zone will react out essentially all of the butenes so that the lower side cut stream 54 from the isostripper will have a very high concentration of normal butane for the return to the dehydrogenation zone. Similarly, the alkylation zone reacts out essentially all the entering propylene so that normal paraffins predominates the content of line 75. In this way, the alkylation zone compliments the operation of the dehydrogenation zone by providing it with a high concentration of saturated components.

Figure 2:
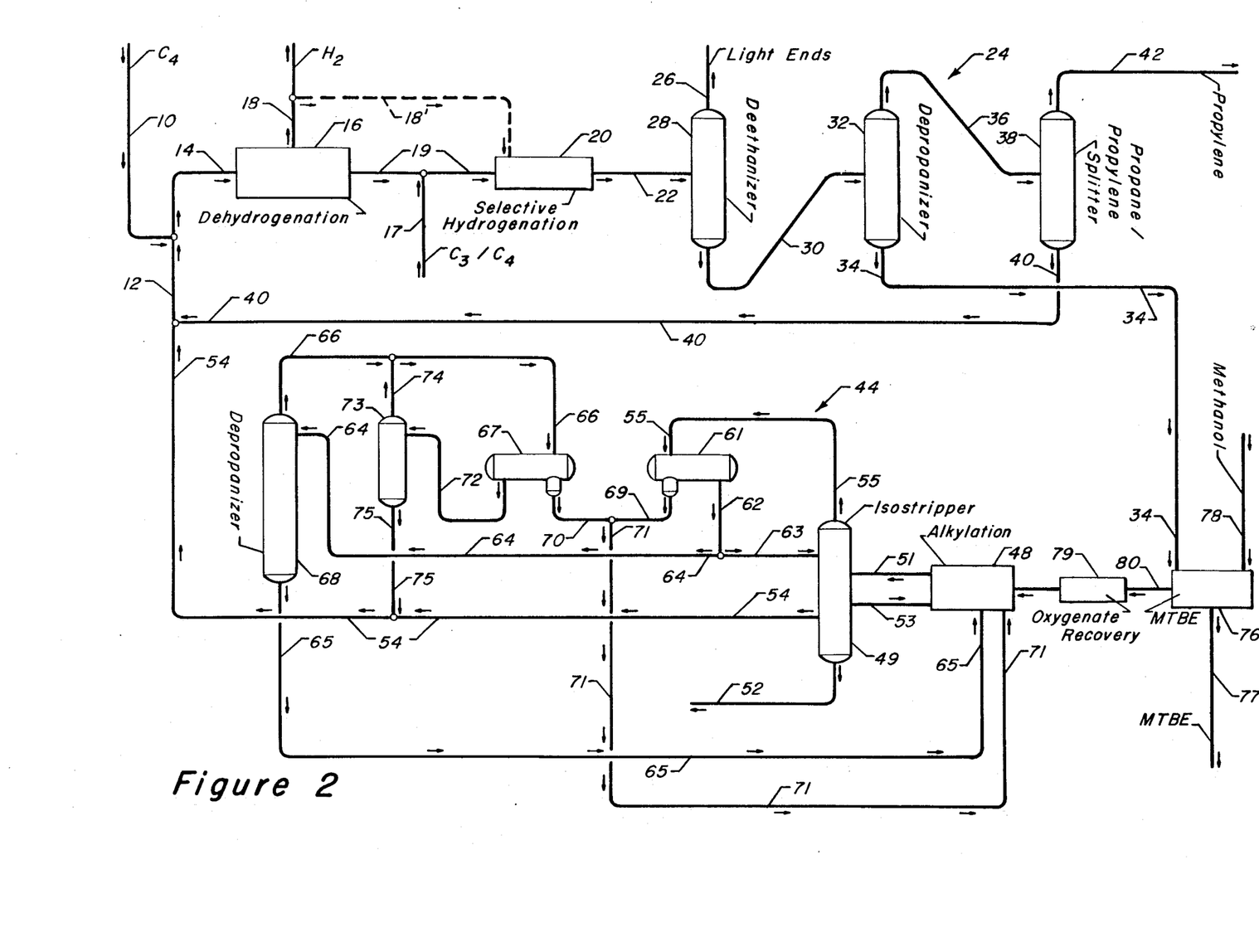
FIG. 2 shows the process as the depicted in FIG. 1 with the addition of etherification facilities.

In order to provide additional products or more effectively utilize isobutene that is produced by the process or enters with the feed components, facilities for etherification may be added to the process. FIG. 2 shows the integration of an etherification zone 76. In the etherification zone, isobutylene is reacted with a monohydric alcohol having from 1–5 carbon atoms. The preferred etherification process is one for the production of methyl-tertiary-butyl ether (MTBE). Several suitable etherification processes have been described in the available literature, with these processes being presently used to produce MTBE. The preferred form of the etherification zone is similar to that described in U.S. Pat. No. 4,219,678 and shown in the previously cited paper. In this instance, isobutylene is transferred to MTBE zone 76 by line 34 while methanol or other feed alcohol are passed into the MTBE zone by line 78 and contacted with an acidic catalyst while maintained at etherification conditions.

A wide range of materials are known to be effective as etherification catalysts for the preferred reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those cross-linked with divinylbenzene. Further information on suitable etherification catalysts may be obtained by reference to U.S. Pat. Nos. 2,480,940, 2,922,822, and 4,270,929 and the previously cited etherification references.

A broad range of suitable etherification conditions includes a superatmospheric pressure sufficient to maintain the reactants as a liquid phase, generally below about 200 bars, and a temperature between about 30° C. (85° F.) and about 100° C. (210° F.). Due to the presence of additional light materials, pressures in the range of 10–40 bars are preferred. A preferred temperature range is from 50° C. (120° F.) to 100° C. (210° F.). The reaction rate is normally faster at higher temperatures but conversion is more complete at lower temperatures. High conversion in a moderate volume reaction zone can, therefore, be obtained if the initial section of the reaction zone, e.g. the first two-thirds, is maintained above 70° C. and the remainder of the reaction zone is maintained below 50° C. This may be accomplished mos easily with two reactors. The ratio of feed alcohol to isoolefin should normally be maintained in the broad range of 1:1 and 1.5:1. An excess of methanol above that required to achieve satisfactory conversion at good selectivity should be avoided. Separation facilities are provided within the etherification zone for the removal of oxygenate compounds.

The MTBE zone will contain a reactor section and a separation section (not shown). The effluent from the reactor section is passed to the separation section for the recovery of an MTBE product through line 77, the recycle of unreacted methanol to reactor section and the production of an alkylation zone feed stream comprising unreacted isobutane and butene. Additional information on the arrangement and construction of the reactor and separation section can be obtained from the previously cited patents.

The alkylation zone feed stream is carried from MTBE section 76 to an oxygenate recovery unit (ORU) 79 by line 80. Oxygenate compound that could interfere with the operation of the other process units or contaminate the products obtained therefrom are separated by methods such as extraction or adsorption and removed from the process by line 82. Effluent from the ORU 78 enters alkylation zone 44 via line 34 in the manner previously described.

EXAMPLES 1-2

The following examples demonstrate the preferred embodiments of this invention as depicted by FIGS. 1 and 2. The description of this invention in terms of this specific process examples is not meant to limit this invention to the particular details disclosed herein. These examples are based on engineering calculations and experience with the operation of similar process units. The drawings provide schematic representation of these types of operation. The drawings show only those portions of the process equipment that are useful in the description of the process. The utilization of other hardware such as compressors, coolers, heaters, valves, reboilers, pumps, instrumentation, and controls have been omitted as not essential to a clear understanding of the process, the use of such hardware being well within the purview of one skilled in the art.

In Example 1, field butanes at a rate of 8059 lbs/hr of isobutane and 19,520 lbs/hr are combined with a propane recycle stream and an alkylation zone recycle. The resulting stream has the composition given under line 14 in Table 1 and is charged to a dehydrogenation zone. Contact with a catalyst composition comprising platinum, lithium and tin on an alumina base, dehydrogenates the butane and propane components of the feed. After passing the feed through the dehydrogenation zone, the dehydrogenation effluent is combined with a $C_3/C_4$ hydrocarbon cut from an FCC unit having the composition given under line 17. The combined stream is passed through a selective hydrogenation zone where it is contacted with a catalyst comprising tin, nickel, and sulfur on an alumina support. The selectively hydrogenated feed from the dehydrogenation zone has the composition given under line 22 in Table 1. In addition, a net hydrogen containing overhead is recovered from the dehydrogenation section and has the composition given under line 18. A total of 35 lbs/hr of hydrogen was removed from this overhead to provide the needed hydrogen for the selective hydrogenation zone.

TABLE 1

| COMPONENT LBS/HR | 14 | 17 | 18 | 22 | 40 |
|---|---|---|---|---|---|
| Hydrogen | 0 | 0 | 930 | — | 0 |
| Methane | 0 | 0 | 800 | 330 | 0 |
| $C_2$ Hydrocarbons | — | 0 | 140 | 1590 | — |
| Propylene | 1,590 | 18,320 | 20 | 27,980 | 1,600 |
| Propane | 24,300 | 7,430 | 20 | 24,170 | 21,700 |
| isobutane | 8,090 | 13,410 | 0 | 17,540 | 26 |
| Isobutene | 10 | 6,850 | 0 | 10,330 | 10 |
| Butene-1 | — | 5,820 | 0 | 5,440 | — |
| Butadiene | — | 233 | 0 | — | — |
| Butene-2 | — | 13,150 | 0 | 29,710 | 0 |
| Normal Butane | 42,310 | 42,310 | 3,770 | 26,300 | 0 |
| Isopentane | 0 | 1,010 | | 1,010 | 0 |

The selective hydrogenation effluent is separated in a deethanizer into a deethanizer overhead stream that contains essentially all of the methane and $C_2$ hydrocarbons along with less than 10 lbs/hr of $C_3$ and heavier hydrocarbons. As mentioned previously, the deethanizer column can be placed either upstream or downstream of the selective hydrogenation zone. Except for about 40 lbs/hr of the mixed $C_4$ hydrocarbons, all of the $C_4$'s in the deethanized selective hydrogenation zone effluent. 1400 lbs/hr propylene, and 2420 lbs/hr of propane are taken from the depropanizer as a bottoms stream to provide part of the alkylation zone feed. Overhead from the depropanizer enters a propane/propylene splitter and is split into 25,000 lbs/hr of a propylene product stream containing only 65 lbs/hr of propane and 12 lbs/hr of ethane and propane recycle stream of having the composition given under line 40 in Table 1.

The depropanizer bottoms stream is combined with 33,000 lbs/hr of make-up isobutane to provide the complete feed to an HF type alkylation zone. The effluent from the alkylation reactor section enters an isostripper which internally recycles an isobutane rich $C_4$ stream to the alkylation reactor section, provides an alkylate product stream and provides an overhead stream containing propane for recycle. 93,000 lbs/hr of alkylate product comprising highly branched $C_7$ and heavier hydrocarbons are recovered in the product stream along with 4,380 lbs/hr of normal butane and 3,390 lbs/hr of isopentane. After further separation for recovery of propane and combination with the isobutane rich $C_4$ stream, the dehydrogenation recycle contains 2,610 lbs/hr of propane and 22,800 lbs/hr of normal butane. The dehydrogenation zone recycle is combined with the propane recycle stream and the field butanes to provide the previously described feed stream carried by line 14.

Example 2 consists of a process arrangement, using the same arrangement and types of processing units of Example 1 with the addition of an MTBE zone for producing an either product. In this case, field butanes consisting of 13,430 lbs/hr of isobutane and 32,530 lbs/hr of normal butane are combined with a propane and alkylation zone recycle to provide a dehydrogenation zone feed having the composition given under line 14. After passage through the dehydrogenation zone, the dehydrogenation zone effluent is recovered and combined with an FCC $C_3/C_4$ cut having the composition given under line 16 in Table 1.

TABLE 2

| COMPONENT LBS/HR | 14 | 18 | 22 | 34 |
|---|---|---|---|---|
| Hydrogen | 0 | 1,360 | — | 0 |
| Methane | 0 | 1,190 | 500 | 0 |
| $C_2$ Hydrocarbons | — | 210 | 2,300 | 0 |
| Propylene | 1,660 | 20 | 29,150 | 1,460 |
| Propane | 26,320 | 20 | 26,190 | 2,620 |
| Isobutane | 13,460 | 0 | 20,290 | 20,260 |
| Isobutene | 10 | 0 | 12,640 | 380 |
| Butene-1 | — | 0 | 7,260 | 7,250 |
| Butadiene | — | 0 | — | — |
| Butene-2 | 0 | 0 | 3,400 | 38,400 |
| n-Butane | 70,190 | 0 | 41,150 | 41,150 |
| Isopentane | 0 | 0 | 1,010 | 1,010 |

A net hydrogen stream having the composition given in Table 2 under line 18 is withdrawn from the dehydrogenation zone. 50 lbs/hr of hydrogen from the net hydrogen stream is added to combined dehydrogenation effluent and FCC cut which enter the selective hydrogenation zone. The selective hydrogenation zone effluent has the composition given under line 22 of Table 2. A deethanizer withdraws 500 lbs/hr of methane, 2,280 lbs/hr of $C_2$ hydrocarbons and 10 lbs/hr of $C_3$ and heavier hydrocarbons from the selective hydrogenation zone effluent. Except for about 50 lbs/hr of mixed $C_4$'s, all of $C_4$ hydrocarbons, 1,460 lbs/hr of propylene, and 2,620 lbs/hr of propane are withdrawn from the bottom of the depropanizer column as part of the feed for the MTBE zone. Overhead from the depropanizer column is split into a propylene product stream containing 26,020 lbs/hr of propylene, 20 lbs/hr of $C_2$ and lighter hydrocarbons, and 70 lbs/hr of propane and a propane recycle containing 23,500 lbs/hr of propane, 1,660 lbs/hr of propylene, and 50 lbs/hr of mixed $C_4$ hydrocarbons. The depropanizer bottoms stream is combined with 6,980 lbs/hr of methanol and about 50 lbs/hr of water to make-up the combined feed for the MTBE zone. The MTBE feed contacts a sulfuric resin catalyst in the MTBE reactor section which produces an effluent from which an MTBE product stream comprising 19,080 lbs/hr of MTBE, 130 lbs/hr of tertiary butyl alcohol, and 1,000 lbs/hr of isopentane is withdrawn. After removal of about 30 lbs/hr of water and dimethyl ether in an oxygenate recovery zone, the remainder of the MTBE effluent is used as part of the feed to the alkylation zone and has the composition given under line 34 of Table 2. Combining the remaining etherification zone effluent with 30,950 lbs/hr of make-up isobutane provides the 10 feed for the HF alkylation zone. Separation of the HF alkylation zone effluent in the isostripper again provides an internal isobutane recycle to the alkylation zone reactor section, an alkylate product stream and recycle streams. The alkylate product stream included 95,090 lbs/hr of highly branched $C_7$ and higher hydrocarbons, 2,430 15 lbs/hr of isopentane and 4,370 lbs/hr of normal butane. Recycle from the alkylation zone consisting of 2,820 lbs/hr of propane and 37,660 lbs/hr of normal butane are combined with the propane recycle and the field butane to form the feed stream to the dehydrogenation zone.

What is claimed is:

1. A process for the production of propylene an high octane blending components from $C_3$ and $C_4$ hydrocarbons, said process comprising:
   (a) passing a first feed stream of combined $C_3$ and $C_4$ hydrocarbons to a dehydrogenation zone and contacting said feed stream with a dehydrogenation catalyst at dehydrogenation conditions to produce a first effluent containing $C_3$ and $C_4$ olefins;
   (b) admixing said first effluent with a second feed stream comprising paraffins and olefins having from 3-4 carbon atoms to form an intermediate stream;
   (c) passing said intermediate stream to a separation zone, recovering a first product stream consisting essentially of propylene, producing a third feed stream comprising $C_3$ and $C_4$ hydrocarbons and producing a first recycle stream comprising propane;
   (d) passing said third feed stream to an alkylation zone with a fourth feed stream comprising isobutane and contacting said third and fourth feeds with an alkylation catalyst at alkylation conditions to produce a second efluent containing high octane blending components comprising $C_7$ and $C_8$ hydrocarbons;
   (e) separating said second effluent from said alkylation zone and recovering a second product stream comprising said $C_7$ and $C_8$ hydrocarbons and a second recycle stream rich in normal butane;
   (f) combining said first recycle stream, said second recycle stream, and a fifth feed stream of $C_4$ paraffins to form said first feed stream.

2. The process of claim 1 wherein said intermediate stream, before entering said separation zone, is contacted with a selective hydrogenation catalyst at selective hydrogenation conditions to saturate diolefins.

3. The process of claim 2 wherein a light hydrocarbon cut from a fluid catalyst cracking unit supplies said additional $C_3$ and $C_4$ hydrocarbons.

4. The process of claim 1 wherein said fourth feed stream comprises at least 80 mol % isobutane.

5. The process of claim 1 wherein said dehydrogenation zone contains a platinum group component, an alkali metal component and a porous inorganic carrier.

6. The process of claim 2 wherein said selective hydrogenation zone contains a catalyst comprising a sulfide high nickel catalyst on an alumina base.

7. The process of claim 1 wherein said separation zone includes a deethanizer column, a depropanizer column, and a propane/propylene splitter, said $C_2$ hydrocarbons and lower boiling materials are withdrawn as the deethanizer overhead, said second feed stream is withdrawn as a bottoms stream of said depropanizer, said first recycle steam is withdrawn as the bottoms stream of said propane/propylene splitter and said first product stream is withdrawn as the overhead of said propane/propylene splitter.

8. The process of claim 1 wherein said second effluent enters an isostripper column, said second product stream and third recycle stream are recovered from said isostripper column along with a fourth recycle stream consisting essentially of isobutane, and said fourth recycle stream is combined with said third and fourth feed streams to provide a combined feed to said alkylation zone having an isobutane to normal butane ratio of at least 6:1.

9. The process of claim 1 wherein said third feed stream is transferred directly from said separation zone to an etherification zone, a $C_1$–$C_5$ alcohol is passed to said etherification zone, said alcohol and said third feed stream are contacted in said etherification zone with an etherification catalyst at etherification conditions, the effluent from said etherification zone is separated into a fifth feed stream comprising $C_3$ and $C_4$ hydrocarbons that pass through an oxygenate removal zone and into said alkylation zone, and a third product stream comprising an ether that is suitable for use as a high octane blending component.

10. The process of claim 9 wherein the alcohol passed to said etherification zone is methanol and said third product stream comprises methyltertiary butyl ether (MTBE).

11. A process for the production of propylene and high octane blending components from $C_3$ and $C_4$ hydrocarbons, said process comprising:
   (a) combining a stream comprising $C_4$ paraffins with a first recycle and a second recycle stream to make up a first feed stream;
   (b) passing said first feed stream to dehydrogenation zone and contacting said feed stream with a dehydrogenation catalyst at dehydrogenation conditions to produce a first effluent comprising $C_3$ and $C_4$ olefins;
   (c) passing said first effluent stream and a second feed stream comprising $C_3$ and $C_4$ hydrocarbons to a selective hydrogenation zone and contacting said streams with a selective hydrogenation catalyst at selective hydrogenation conditions to produce a second effluent stream substantially free of olefins;

(d) passing said second effluent to a deethanizer column to remove any $C_2$ or lower boiling materials that are present in said second effluent as a result of steps (a), (b) and (c);

(e) passing the remainder of said second effluent from said deethanizer column to a depropanizer column and recovering a third feed stream rich in $C_4$ hydrocarbons;

(f) passing the remainder of said second effluent from said depropanize to a propane/propylene splitter and recovering a first product stream comprising high purity propylene and said first recycle stream comprising propane;

(g) passing said third feed stream and a fourth feed stream comprising isobutane to an alkylation zone and contacting said third and fourth feed streams with an alkylation catalyst at alkylation conditions; and recovering a third effluent from said alkylation zone; and (h) separating said third effluent into a second product stream comprising branched $C_7$ and $C_8$ paraffins and said second recycle stream comprising $C_4$ hydrocarbons.

12. The process of claim 11 wherein said fourth feed stream comprises at least 90 mol % isobutane.

13. A process for the production of propylene and high octane blending components said process comprising:

(a) combining a stream comprising $C_4$ paraffins with a first recycle and a second recycle stream to make up a first feed stream;

(b) passing said first feed stream to a dehydrogenation zone and contacting said feed stream with a dehydrogenation catalyst at dehydrogenation conditions to produce a first effluent comprising $C_3$ and $C_4$ olefins;

(c) passing said first effluent stream and a second stream comprising $C_3$ and $C_4$ hydrocarbons to a selective hydrogenation zone and contacting said streams with a selective hydrogenation catalyst at selective hydrogenation conditions to produce a second effluent stream substantially free of diolefins;

(d) passing said second effluent to a deethanizer column to remove any $C_2$ or lower boiling materials that are present in said second effluent as a result of steps (a), (b) and (c);

(e) passing the remainder of said second effluent from said deethanizer column to a depropanizer column and recovering a third feed stream rich in $C_4$ hydrocarbons;

(f) passing the remainder of said second effluent from said depropanizer to a propane/propylene splitter and recovering a first product stream comprising high purity propylene and said first recycle stream comprising propane;

(g) passing said third feed stream and a $C_1$–$C_5$ alcohol to an etherification zone, contacting said third feed stream and said alcohol in said etherification zone at etherification zone conditions, recovering a third effluent stream from said etherification, separating and recovering a second product stream comprising a high octane ether from said third effluent stream and passing the remainder of said third effluent stream through an oxygenate removal zone;

(h) passing the remainder of said third effluent from said oxygenate removal zone and a fourth feed stream comprising isobutane to an alkylation zone, contacting said third effluent stream and fourth feed stream with an alkylation catalyst at alkylation conditions and recovering a fourth effluent stream; and (i) separating said fourth effluent into said second recycle comprising $C_3$ hydrocarbons and $C_4$ normal hydrocarbons and a third product stream comprising branched $C_7$ and $C_8$ paraffins.

14. The process of claim 13 wherein said alcohol is methanol and said second product stream comprises methyl-tert-butyl ether (MTBE).

15. The process of claim 14 wherein said fourth product stream comprises at least 90 mol % isobutane.

* * * * *